United States Patent [19]
Cody et al.

[11] Patent Number: 5,916,590
[45] Date of Patent: Jun. 29, 1999

[54] SOFT GELATIN PHARMACEUTICAL DOSAGE FORM

[75] Inventors: Sharon L. Cody, Philadelphia; Michael R. Hoy, Sellersville; Edward J. Roche, Paoli; Eric J. Walter, Philadelphia, all of Pa.

[73] Assignee: McNeil-PPC, Inc., Skillman, N.J.

[21] Appl. No.: 08/719,739

[22] Filed: Sep. 25, 1996

Related U.S. Application Data

[63] Continuation of application No. 08/366,945, Dec. 29, 1994, abandoned.

[51] Int. Cl.$^6$ .................................................. A61K 9/48
[52] U.S. Cl. ........................ 424/452; 424/454; 424/455; 424/456; 514/944; 514/772.3; 514/784
[58] Field of Search ................................ 424/455, 456, 424/451, 452, 454, 453

[56] References Cited

U.S. PATENT DOCUMENTS

| | | | |
|---|---|---|---|
| 1,970,396 | 8/1934 | Scherer | 18/21 |
| 2,288,327 | 6/1942 | Scherer | 18/21 |
| 2,318,718 | 5/1943 | Scherer | 18/21 |
| 3,851,051 | 11/1974 | Miskel et al. | 424/37 |
| 3,903,008 | 9/1975 | Deweever et al. | 252/118 |
| 4,028,024 | 6/1977 | Moreland | 425/133.1 |
| 4,428,927 | 1/1984 | Ebert et al. | 424/37 |
| 4,467,921 | 8/1984 | Greenleaf et al. | 206/524.4 |
| 4,486,412 | 12/1984 | Shah et al. | 424/156 |
| 4,609,403 | 9/1986 | Wittwer et al. | 106/122 |
| 4,690,822 | 9/1987 | Uemura et al. | 424/455 |
| 4,708,834 | 11/1987 | Cohen et al. | 264/4.3 |
| 4,727,109 | 2/1988 | Schmidt et al. | 424/455 |
| 4,795,642 | 1/1989 | Cohen et al. | 424/455 |
| 4,844,906 | 7/1989 | Hermelin et al. | 424/454 |
| 4,883,660 | 11/1989 | Blackman et al. | 424/78 |
| 4,935,243 | 6/1990 | Borkan et al. | 424/441 |
| 5,071,643 | 12/1991 | Yu et al. | 514/570 |
| 5,085,033 | 2/1992 | Graham | 53/436 |
| 5,146,730 | 9/1992 | Sadek et al. | 53/454 |
| 5,505,961 | 4/1996 | Shelley et al. | 242/451 |

FOREIGN PATENT DOCUMENTS

| | | |
|---|---|---|
| 0 107 330 A3 | 5/1984 | European Pat. Off. . |
| 0 225 848 A3 | 6/1987 | European Pat. Off. . |
| 298351 A5 | 2/1992 | Germany . |
| 4201178 A1 | 7/1993 | Germany . |
| 88/02625 | 4/1988 | WIPO . |
| 91/07950 | 6/1991 | WIPO . |
| 95/04527 | 2/1995 | WIPO . |

OTHER PUBLICATIONS

Dialog Abstract for France 2,135,257, Dec. 15, 1972.
Dialog Abstract for Germany, 26 07 849, May 26, 1977.
Dialog Abstract for EPO 0 461 290, Feb.18, 1991.
Handbook of Pharmaceutical Excipients, Amer. Pharm. Assn/Pharmaceutical Soc. of Great Britian, pp. 234–239, (1986).
The U.S. Pharmacopeia, The National Formulary, USP 23 NF 18 pgs. 1830–1835 (1995).
H. Seager, Pharmaceutical Technology, Sep. 1985, Soft Gelatin Capsules: A Solution to Many Tableting Problems, pp. 84,86,88,90,92,94,96,98,100,102,& 104.
Remington's Pharmaceutical Sciences, 18th Ed. Chap. 83, pp. 1539–1540 (1990).

*Primary Examiner*—Thurman K. Page
*Assistant Examiner*—James M. Spear
*Attorney, Agent, or Firm*—Bernard F. Plantz

[57] ABSTRACT

The present invention relates to a substantially translucent, gel fill material for a soft gelatin capsule containing a therapeutically effective amount of a pharmaceutical dissolved or suspended in the gel. The gel is sufficiently viscous so that it cannot be expelled at room temperature from the capsule with a syringe.

26 Claims, No Drawings

SOFT GELATIN PHARMACEUTICAL DOSAGE FORM

This is a continuation of application Ser. No. 08/366,945, filed Dec. 29, 1994 abandoned.

FIELD OF THE INVENTION

The present invention relates to a soft gelatin capsule filled with a gel containing a therapeutically effective amount of a pharmaceutical dissolved or suspended in the gel and, more particularly, to a gel fill material that has a substantially translucent appearance.

BACKGROUND OF THE INVENTION

In recent years soft gelatin or soft elastic gelatin capsules have become a popular dosage form for the oral delivery of therapeutic agents, especially over-the-counter pharmaceuticals. These capsules are typically filled with a liquid containing the active ingredient. Because of their soft, elastic character, some patients view these capsules as easier to swallow than conventional tablets or hard gelatin capsules. Since the dosage form is generally swallowed, it is not necessary to flavor or otherwise mask the often unpleasant taste of the pharmaceutical. Soft gelatin capsules are also preferred to bulk liquids because they are easier to transport and they avoid the need for the patient to measure a prescribed amount of the liquid before dosing.

The fill material used in a soft gelatin capsule generally contains a pharmaceutical dissolved or dispersed in a carrier that is compatible with the capsule wall. In addition to liquids, U.S. Pat. No. 4,935,243 to L. Borkan et al. suggests that the fill material may take the form of a semi-solid, solid, or gel. Conventional tablets or pellets containing an active ingredient are examples of solid fill materials that may be encapsulated within a soft gelatin capsule.

Semi-solid (dispersion) fill material are discussed in U.S. Pat. No. 4,486,412 to D. Shah et al. A fill material containing an orally-administered antacid salt that is dispersed in a water-free, liquid carrier containing a major proportion of one or more polyalkylene glycols and a minor proportion of a $C_2$–$C_5$ polyol, such as propylene glycol or glycerin. The carrier forms a stable dispersion of the antacid salt and coats the antacid particles, thereby rendering them non-reactive with the soft gelatin capsule wall.

U.S. Pat. No. 4,708,834 to Cohen et al. suggests a controlled release pharmaceutical dosage form comprising a soft gelatin capsule that encloses a water-soluble or dispersible gelled polymer matrix. The fill material comprises an aqueous solution or dispersion of a polysaccharide gum, the pharmaceutical active and, optionally, an alcohol. The liquid fill is introduced into a soft gelatin capsule that contains a cationic gelling agent, which gels the liquid fill after it has been incorporated into the capsule shell. The alcohol used in the fill includes liquid polyethylene glycols, lower alkanols, $C_2$–$C_4$ polyols and mixtures thereof.

U.S. Pat. No. 5,071,643 to M. Yu et al. also discusses the use of polyethylene glycols (PEG) as a fill material in soft gelatin dosage forms. PEGs having an average molecular weight between 400–600 are preferred for liquid fills, between 800–10,000 for semi-solid fills and between 10,000–100,000 for solid fills.

*Remington's Pharmaceutical Sciences,* 18th ed, Chapter 83, pp. 1539–40 (1990), reports that gelling agents used to make gels for pharmaceutical and cosmetic products, include sodium alginate and triethanolamine.

PCT Publication No. WO 91/07950 describes a soft or two-piece hard gelatin capsule shell containing benzodiazepine dissolved or suspended in a gel. The gel contains by weight at least 63% of polyethylene glycol 600, at least 4% of polyethylene glycol 4000 or 6000, and at least 21% of polyethylene glycol 600–4000. This gel fill cannot be expelled with a syringe at ambient temperature and therefore avoids the reported abuse of liquid filled capsules by intravenous drug abusers. As reported in Example 1 of the present application, gels containing this blend of polyethylene glycols have an opaque appearance.

A need exists for a substantially translucent, gel fill material suitable for use in the production of soft gelatin capsules. The fill material should also be sufficiently viscous so as to prevent it from being expelled from the capsule shell with a syringe.

SUMMARY OF THE INVENTION

The present invention provides a fill material for a soft gelatin capsule comprising a polyalkylene glycol having an average molecular weight of about 600 or less, water and a gelling agent in an amount effective to gel the glycol. A therapeutically effective amount of a pharmaceutical is dissolved or suspended in said gel, and the resulting gel has a turbidity of less than about 1300 NTU (Nephelometric Turbidity Unit)

The gel of the present invention has a substantially translucent appearance, and when used to fill a soft gelatin capsule, which is also translucent, the resulting dosage form has an elegant, substantially translucent or clear appearance.

In A further embodiment of the present invention, the gel is sufficiently viscous so that it cannot be expelled at room temperature from the capsule with a syringe, preferably having an 18 gauge or smaller needle.

DETAILED DESCRIPTION OF THE PREFERRED EMBODIMENTS

The present invention relates to a substantially translucent gel for filling a soft gelatin capsule pharmaceutical dosage form. The gel may also be used to fill a two-piece hard gelatin capsule. The viscosity of the gel is also controlled so that it cannot be readily removed from the capsule with a syringe at room temperature. This feature helps to protect against possible intravenous abuse of the drug as well as product tampering.

The solvent used in the gel of the present invention is a pharmaceutically acceptable material which gels to produce a substantially translucent gel. Suitable solvents include liquid polyalkylene glycols having an average molecular weight of about 600 or less. The solvent is preferably a liquid polyethylene glycol having an average molecular weight of about 200 to about 600, most preferably about 300 to about 400. A minor proportion of water is also used in conjunction with the solvent. The gel generally comprises by weight about 35 to about 95 percent solvent and about 5 to about 25 percent water. Unless otherwise stated, the percentages recited herein are by weight of the total weight of the gel fill material, i.e., both the gel and active ingredient.

The gelling agent used in the present invention includes sodium stearate, sodium palmitate, and calcium acetate. With the exception of calcium acetate, it is necessary to heat the solvent, water and the gelling agent to an elevated temperature, e.g, boiling, and then allow the resulting mixture to cool to room temperature in order to effect gelling. It has, however, been unexpectedly discovered that the solvent can be gelled with calcium acetate at room temperature. Further details of the use of calcium acetate as a gelling agent may be found in copending, commonly assigned patent application Ser. No. 08/366,271, filed on even date herewith, entitled "Gelling Agent for Polyethylene Glycol," which is hereby incorporated by reference.

In a preferred embodiment, the gelling agent is employed in an amount effective to form a gel that is substantially translucent and is sufficiently viscous so that it cannot be expelled at room temperature with a syringe having an 18 gauge or smaller needle. Generally the gel contains by weight from about 0.25 to about 5 percent of one or more of sodium stearate, sodium palmitate, and calcium acetate.

It has also been discovered that it is advantageous to add sodium acetate to the gel to enhance its clarity, especially when sodium stearate or sodium palmitate is used as the gelling agent. Sodium acetate is used in an amount that produces the desired clarity, generally from about 2 to about 20 percent by weight.

Solubilizing agents may also be employed to enhance the solubility or dispersibility of the active ingredient in the gel. Suitable agents include glycerin, ethanol, propylene glycol, N-methyl-2-pyrrolidone, dimethyl isosorbide, povidone (PVP) and other pharmaceutically acceptable surfactants, each ranging in amount from 0 to about 15 percent by weight of the gel.

The strength or rigidity of the gel can be increased with the addition of one or more of the following strength enhancing agents in the amount shown (% by wt. of gel):

| % | Component |
|---|---|
| 0.05–2 | Poloxamer |
| 0.05–5 | Hydroxyethyl cellulose |
| 0.05–5 | Ethylcellulose |
| 0.05–5 | Methylcellulose |
| 0.05–5 | Polyvinyl Alcohol |
| 0.05–5 | Hydroxypropyl methylcellulose |
| 0.05–15 | Sorbitol. |

Preferred poloxamers (poly (oxyethylene)-poly (oxypropylene) copolymer) include Poloxamer 188, Poloxamer 237, and Poloxamer 407.

If acetaminophen is used as the active ingredient, it may desirable to include an antioxidant to eliminate "pinking."

The pharmaceutical active used in the present invention can be any medication which can be administered orally to transmit the active agent into the gastrointestinal tract and into the bloodstream at therapeutically effective levels. The medication, at the desired dosage, must also be sufficiently soluble or dispersible in the gel so that the resulting composition has a turbidity of less than about 1300, preferably less than about 700, NTU.

The pharmaceutical active(s) is present in the dosage form in a therapeutically effective amount, which is an amount that produces the desired therapeutic response upon oral administration, and can be readily determined by one skilled in the art. In determining such amounts, the particular compound being administered, the bioavailability characteristics of the compound, the dose regime, the age and weight of the patient, and other factors must be considered. Pharmaceuticals suitable for use in the invention include acetaminophen, famotidine, chlorpheniramine, pseudoephedrine, dextromethorphan, diphenhydramine, brompheniramine, clemastine, phenylpropanolamine, terfenadine, astemizole, loratadine, pharmaceutically acceptable salts thereof and mixtures thereof. Generally, the pharmaceutical comprises about about 0.1 to about 40, preferably about 0.2 to about 30, percent by weight of the total gel composition.

Various other pharmaceutically acceptable excipients may be included in the dosage form, such as preservatives, e.g., methyl- or propylparaben, and coloring agents.

In a preferred embodiment, a fill for a soft gelatin capsule containing about 325 mg/ml acetaminophen, comprises by weight about 20 to about 35 percent acetaminophen, about 40 to about 70 percent polyethylene glycol having an average molecular weight of about 400, about 5 to about 15 percent water, about 2 to about 10 percent sodium acetate, about 0.5 to about 1.5 percent sodium stearate, and from about 0.05 to about 0.3 percent poloxamer.

In a preferred embodiment, a fill for a soft gelatin capsule containing about 250 mg/ml acetaminophen, comprises by weight from about 23 to about 27 percent acetaminophen, from about 55 to about 65 percent PEG 400, from about 10 to about 20 percent water, from about 2 to about 10 percent sodium acetate, from about 0.25 to about 1.5 percent sodium stearate and from about 0.05 to about 0.3 percent poloxamer. Optionally, if a combination cough-cold product is being the formulated, the fill may further comprise by weight one or more of about 2.5 to about 3.5 percent pseudoephedrine HCl, about 1 to about 2 percent dextromethorphan HBr, and about 0.1 to about 0.3 chlorpheniramine maleate.

In a further preferred embodiment, a fill for a soft gelatin capsule containing about 250 mg/ml of acetaminophen, comprises by weight from about 23 to about 27 percent acetaminophen, from about 60 to about 70 percent PEG 400, from about 10 to about 20 percent water, and from about 1 to about 3 percent calcium acetate.

In a still further preferred embodiment, a fill for a soft gelatin capsule containing from 10–40 mg/mL famotidine, comprises by weight about 0.5 to about 5 percent famotidine, from about 60 to about 70 percent PEG 400, from about 10 to 20 percent water, from about 2 to about 10 percent sodium acetate, from about 0.5 to about 1.5 percent sodium stearate and from about 0.05 to about 0.3 percent poloxamer.

The fill material of the present invention may be used in commercially available soft gelatin capsules, such as those commercially available from R. P. Scherer or Banner Pharmacaps. Various sizes, shapes, and colors can be used to accommodate different levels of active ingredients. The walls of the capsules have a substantially translucent or clear appearance. When the fill material of the present invention is introduced into the capsule and gelled, the resulting dosage form has an elegant, translucent or clear appearance.

The fill material is heated before it is loaded into the capsule because it generally gels at temperatures below 40° C. Air-filled soft gelatin capsules can be used to hand fill capsules with a syringe. The hot liquid fill is loaded into a syringe. The needle on the syringe is used to puncture one end of the soft gelatin capsule so that the appropriate amount of fill material may be injected by hand. The capsule with fill material is allowed to cool to ambient room temperature.

The fill material may also be introduced into the soft gelatin capsule using encapsulation equipment known in the art, such as that described in U.S. Pat. No. 4,028,024 to Moreland, which is hereby incorporated by reference. As previously described with the hand-filling technique, the fill must be maintained at above about 40° C. during the filling operation so that it readily flows into the capsule. Therefore, the fill can be stored in a jacketed vessel and transported through a thermostatically controlled feeding tube to the encapsulation equipment.

Specific embodiments of the present invention are illustrated by way of the following examples. This invention is not confined to the specific limitations set forth in these examples, but rather to the scope of the appended claims. Unless otherwise stated, the percentages and ratios given below are by weight of the total composition.

The turbidity of the fill materials described in the following examples was measured using a Hach Ratio/XR Turbidimeter. The United States Pharmacopedia defines turbidance as the light-scattering effect of suspended particles and turbidity as the measure of the decrease in the incident beam intensity per unit length of a given suspension. This instrument measures turbidity within a range of 0.00 to 2000 NTU. As a point of reference, the turbidity of water is zero. Samples of the fill materials, approximately 8 mL, were transferred to Fisher Brand 13×100 mm culture tubes immediately after manufacture. The fill material samples were stored at ambient room temperature since they were made several days in advance. The outer surface of each of the sample culture tubes was treated with silicone oil just prior to measuring the turbidity. The turbidity of the samples was measured at ambient room temperature. The turbidity of two sample tubes of each fill material was measured and the average of the results is reported.

EXAMPLE 1

This Example provides a comparison of the PEG blends similar to those described in PCT Publication WO 91/07950. The following blends were prepared:

|  | Amount (% w/w) | |
| --- | --- | --- |
| Component | Sample A | Sample B |
| PEG 600 | 64.40 | 64.40 |
| PEG 1450 | 26.20 | 26.20 |
| PEG 3500 | — | 4.20 |
| PEG 8000 | 4.20 | — |
| Glycerol | 5.20 | 5.20 |

The samples were prepared as follows:
1) Weigh PEGs and glycerol.
2) Place mixture on preheated hot plate set to highest setting. Mix with heat (approximately 75° C.) until a clear solution is obtained.
3) Remove mixture from heat and mixing. Sonicate with heat temp set=69° C. Upon cooling to RT to form a gel, both Samples had an opaque white appearance with a turbidity exceeding 2000 NTU.

EXAMPLE 2

This Example discloses a fill material of the present invention containing 200 mg/ml of acetaminophen. The fill contained:

| Component | Amount (% w/w) |
| --- | --- |
| Acetaminophen | 17.71 |
| PEG-400 | 63.74 |
| Purified Water | 14.16 |
| Sodium Acetate | 3.54 |
| Sodium Stearate | 0.71 |
| Poloxamer 237 | 0.14 |

The samples were prepared as follows:
1) Weigh sodium acetate and add water. Mix until sodium acetate is dissolved.
2) Add PEG 400.
3) Place mixture on preheated hot plate set to highest setting. Mix for about 3 minutes.
4) Add sodium stearate and increase mixing speed.
5) Let mixture boil with vigorous mixing. Vary heating/mixing times (1,2,4,6,8,10 min).
6) Add Poloxamer 237 and continue mixing for about 1 minute.
7) Add active and continue mixing for about 1 minute.
8) Remove mixture from heat and mixing. Sonicate with heat temp set=69° C. Let mixture cool at RT.

The resulting fill materials could not be expelled at room temperature with a syringe having an 18 gauge needle. Upon gelling, the fill materials were observed to have a substantially clear appearance. The turbidity of the Samples is as follows:

| Sample | Heat (min) | Turbidity (NTU) |
| --- | --- | --- |
| A | 1 | 117.6 |
| B | 2 | 84.2 |
| C | 4 | 70.0 |
| D | 6 | 71.3 |
| E | 8 | 65.6 |
| F | 10 | 59.5 |

EXAMPLE 3

This Example discloses a fill material of the present invention containing 200 mg/ml of acetaminophen and varying amounts of sodium stearate as the gelling agent. The fill material contained:

|  | Amount (% w/w) | | | | |
| --- | --- | --- | --- | --- | --- |
| Component | A | B | C | D | E |
| Acetaminophen | 18.36 | 18.23 | 18.09 | 17.96 | 17.83 |
| PEG 400 | 66.08 | 65.60 | 65.12 | 64.66 | 64.19 |
| Purified Water | 14.68 | 14.57 | 14.47 | 14.36 | 14.26 |
| Sodium Stearate | 0.74 | 1.46 | 2.18 | 2.88 | 3.58 |
| Poloxamer 237 | 0.14 | 0.14 | 0.14 | 0.14 | 0.14 |

The samples were prepared as follows:
1) Weigh PEG 400 and water.
2) Place mixture on preheated hot plate set to highest setting. Mix for about 3 minutes.
3) Add sodium stearate and increase mixing speed.
4) Let mixture boil with vigorous mixing for about 6 minutes.
5) Add Poloxamer and continue mixing for about 1 minute.
6) Add acetaminophen and continue mixing for about 1 minute.
7) Remove mixture from heat and mixing. Sonicate with heat temp set=69° C. Let mixture cool at RT.

Samples B–E could not be expelled at room temperature with a syringe having an 18 gauge needle. Samples A–D were substantially translucent. The Samples had the following turbidity:

| Sample | % NaSt | Turbidity |
| --- | --- | --- |
| A+ | 0.74 | 466 |
| B | 1.46 | 1217 |
| C | 2.18 | 1050 |
| D | 2.88 | 1076 |
| E | 3.58 | >>2000 |

+ = solution/not gelled

EXAMPLE 4

This Example discloses a fill material of the present invention containing 10, 20 and 40 mg/mL of famotidine. The fill material contained:

| | Amount (% w/w) | | |
| --- | --- | --- | --- |
| Component | A | B | C |
| Famotidine | 0.86 | 1.70 | 3.34 |
| PEG 400 | 76.79 | 76.14 | 74.88 |
| Purified Water | 17.06 | 16.91 | 16.63 |
| Sodium Acetate | 4.26 | 4.23 | 4.16 |
| Sodium Stearate | 0.86 | 0.85 | 0.83 |
| Poloxamer 237 | 0.17 | 0.17 | 0.16 |

The samples were prepared as follows:

1) Weigh sodium acetate and add water. Mix until sodium acetate is dissolved.
2) Add PEG 400.
3) Place mixture on preheated hot plate set to highest setting. Mix for about 3 minutes.
4) Add sodium stearate and increase mixing speed.
5) Let mixture boil with vigorous mixing. Mix for about 6 minutes.
6) Add Poloxamer 237 and continue mixing for about 1 minute.
7) Add active and continue mixing for about 1 minute.
8) Remove mixture from heat and mixing. Sonicate with heat temp set=69° C. Let mixture cool at RT.

The resulting fill materials could not be expelled at room temperature with a syringe having an 18 gauge needle. The fill materials were substantially translucent and had the following turbidity:

| Sample | Famotidine (% w/w) | Turbidity (NTU) |
| --- | --- | --- |
| A | 0.86 | 1226 |
| B | 1.70 | 1120 |
| C | 3.34 | 1214 |

EXAMPLE 5

This Example discloses a fill material of the present invention containing 200 mg/mL of acetaminophen which was gelled at room temperature with calcium acetate. The fill material contained:

| Component | Amount (% w/w) |
| --- | --- |
| Acetaminophen | 18.24 |
| PEG 400 | 65.70 |
| Calcium Acetate | 1.46 |
| Purified Water | 14.60 |

The sample was prepared as follows:

1) Weigh calcium acetate and water. Sonicate/mix to dissolve calcium acetate.
2) In a separate beaker, weigh active and PEG 400. Mix to form active/PEG slurry.
3) Add calcium acetate solution to PEG while mixing. Continue to mix until system gels.
4) Sonicate gel to remove air.

The fill material was substantially translucent and had a turbidity of 865 NTU, although some air was noted in the tested samples.

The resulting fill material could be expelled at room temperature with a syringe having an 18 gauge needle because the strength of the gel was weakened by the mixing step. It was found that the gel strength can be maximized by eliminating the mixing step. The sample was prepared a second time by first hand-filling a soft gelatin capsule shell with the active/PEG slurry with a syringe. Then the calcium acetate solution was injected into the capsule shell containing the active/PEG slurry. The resulting mixture was allowed to gel at room temperature in the capsule shell. The capsule was then cut open with a scalpel and the fill material was observed to be a solid material.

EXAMPLE 6

This Example discloses a fill material of the present invention containing 225 mg/mL of acetaminophen, 27 mg/mL of pseudoephedrine HCl and 2 mg/mL of chlorpheniramine maleate. The fill material contained:

| Component | Amount (% w/w) |
| --- | --- |
| Acetaminophen | 19.5 |
| Pseudoephedrine HCl | 2.34 |
| Chlorpheniramine Maleate | 0.16 |
| PEG 400 | 58.5 |
| Purified Water | 15.6 |
| Sodium Acetate | 3.12 |
| Sodium Stearate | 0.78 |

The sample was prepared as follows:

1) Weigh the sodium acetate and add water. Mix until sodium acetate is dissolved.
2) Add PEG 400.
3) Place mixture on preheated hot plate set to highest setting. Mix for about 3 minutes.
4) Add sodium stearate and increase mixing speed.
5) Let mixture boil with vigorous mixing. Mix for about 7 minutes.
6) Add actives and continue mixing for about 1 minute.
7) The resulting mixture was hand filled into a soft gelatin capsule shell using a syringe.

EXAMPLE 7

This Example discloses the results of a syringeability test conducted on a fill materials of the present invention containing acetaminophen. The fill materials contained:

|  | Amount (% w/w) | | |
| --- | --- | --- | --- |
| Component | A | B | C |
| Acetaminophen | 20.0 | 20.0 | 20.0 |
| PEG 400 | 62.4 | 61.6 | 62.0 |
| Purified Water | 8.0 | 8.0 | 8.0 |
| Ethanol | 8.0 | 8.0 | 8.0 |
| Sodium Stearate | 1.6 | 2.4 | 2.0 |

The samples were prepared as follows:
1) Weigh PEG 400, water and ethanol.
2) Place mixture on preheated hot plate set to highest setting. Mix for about 3 minutes.
3) Add sodium stearate and increase mixing speed.
4) Let mixture boil with vigorous mixing. Mix for about 7 minutes.
5) Add active and continue mixing for about 1 minute.
6) Allow the mixture to gel.

The syringeability of the samples was tested using a syringe with an 18 gauge needle. The testing was performed by swiftly pulling the plunger two complete times and then noting if any gel was in the syringe bulb. No gel from Sample B was found in the syringe bulb, but minor amounts of the gel from Samples A and C were detected in the bulb.

It is believed that the addition of a small amount of poloxamer to Samples A and C would result in a gel which would not be draw into the syringe bulb.

Various modifications can be made to the above-described embodiments without departing from the spirit and scope of the present invention.

What is claimed is:

1. A pharmaceutical composition, comprising:
   a gel comprising a polyalkylene glycol having an average molecular weight of about 600 or less, water and a gelling agent in an amount effective to gel said glycol;
   a therapeutically effective amount of a pharmaceutical selected from the group consisting of acetaminophen, famotidine, chlorpheniramine, pseudoephedrine, dextromethorphan, diphenhydramine, brompheniramine, clemastine, phenylpropanolamine, terfenadine, astemizole, loratadine, pharmaceutically acceptable salts thereof and mixtures thereof dissolved or suspended in said gel; and
   said composition having a turbidity less than about 1300 NTU.

2. The composition of claim 1 wherein the turbidity is less than about 700 NTU.

3. The composition of claim 1 comprising:
   about 35 to about 95 percent of polyethylene glycol; and
   about 5 to about 25 percent of water; and
   about 0.25 to about 5 percent of the gelling agent, by weight of the gel.

4. The composition of claim 1 comprising polyethylene glycol having an average molecular weight of about 200 to about 600.

5. The composition of claim 1 wherein the gelling agent is selected from the group consisting of sodium stearate, sodium palmitate, and calcium acetate.

6. The composition of claim 1 further comprising sodium acetate.

7. A pharmaceutical composition, comprising:
   a gel comprising about 35 to about 95 percent of polyethylene glycol;
   about 5 to about 25 percent of water;
   about 0.25 to about 5 percent of the gelling agent, by weight of the gel;
   a therapeutically effective amount of a pharmaceutical dissolved or suspended in said gel; and
   said composition having a turbidity less than about 1300 NTU.

8. The composition of claim 1 comprising sodium stearate and sodium acetate.

9. The composition of claim 1 wherein said gel comprises polyethylene glycol having an average molecular weight of about 300 to about 400, sodium stearate and sodium acetate.

10. The composition of claim 1, comprising by weight:
    about 35 to about 95 percent of polyethylene glycol having an average molecular weight of about 300 to about 400;
    about 5 to about 25 percent of water; and
    about 0.25 to about 5 percent of a gelling agent selected from the group consisting of sodium stearate, sodium palmitate and calcium acetate;
    0 to about 20 percent of sodium acetate; and
    0 to about 2 percent of poloxamer.

11. A pharmaceutical dosage form, comprising:
    a soft gelatin shell filled with a gel containing a therapeutically effective amount of a pharmaceutical selected from the group consisting of acetaminophen, famotidine, chlorpheniramine, pseudoephedrine, dextromethorphan, diphenhydramine, brompheniramine, clemastine, phenylpropanolamine, terfenadine, astemizole, loratadine, pharmaceutically acceptable salts thereof and mixtures thereof dissolved or suspended in said gel, said gel comprising polyalkylene glycol having an average molecular weight of about 600 or less, water and a gelling agent in an amount effective to gel said glycol; and
    said gel containing the pharmaceutical having a turbidity less than about 1300 NTU.

12. The dosage form of claim 11 wherein the turbidity is less than about 700 NTU.

13. A method of delivering a pharmaceutical comprising the oral administration of the dosage form of claim 11.

14. The dosage form of claim 11 comprising:
    about 35 to about 95 percent of polyethylene glycol; and
    about 5 to about 25 percent of water; and
    about 0.25 to about 5 percent of the gelling agent, by weight of the gel.

15. The dosage form of claim 11 comprising polyethylene glycol having an average molecular weight of about 200 to about 600.

16. The dosage form of claim 11 wherein the gelling agent is selected from the group consisting of sodium stearate, sodium palmitate, and calcium acetate.

17. The dosage form of claim 15 further comprising sodium acetate.

18. A pharmaceutical dosage form, comprising:
    a soft gelatin capsule shell filled with a gel comprising about 35 to about 95 percent of polyethylene glycol having an average molecular weight of 60 or less, about 5 to about 25 percent of water, and about 0.25 to about 5 percent of a gelling agent, by weight of the gel;
    a therapeutically effective amount of a pharmaceutical dissolved or suspended in said gel; and said gel containing the pharmaceutical having a turbidity less than about 1300 NTU.

19. The dosage form of claim 11 comprising sodium stearate and sodium acetate.

20. The dosage form of claim 11 wherein said gel comprises polyethylene glycol having an average molecular weight of about 300 to about 400, sodium stearate and sodium acetate.

21. The dosage form of claim 11, comprising by weight:
   about 35 to about 95 percent of polyethylene glycol having an average molecular weight of about 300 to about 400;
   about 5 to about 25 percent of water;
   about 0.25 to about 5 percent of a gelling agent selected from the group consisting of sodium stearate, sodium palmitate and calcium acetate;
   0 to about 20 percent of sodium acetate; and
   0 to about 2 percent of poloxamer.

22. The dosage form of claim 11, comprising by weight:
   about 20 to about 35 percent acetaminophen;
   about 40 to about 70 percent polyethylene glycol having an average molecular weight of about 400;
   about 5 to about 15 percent water;
   about 2 to about 10 percent sodium acetate;
   about 0.5 to about 1.5 percent sodium stearate; and
   from about 0.05 to about 0.3 percent poloxamer.

23. The dosage form of claim 22, further comprising by weight:
   about 2.5 to about 3.5 percent pseudoephedrine HCl;
   about 1 to about 2 percent dextromethorphan HBr; and
   about 0.1 to about 0.3 of chlorpheniramine maleate.

24. The dosage form of claim 11, comprising by weight:
   about 23 to about 27 percent of acetaminophen;
   about 60 to about 70 percent of polyethylene glycol having an average molecular weight of about 400;
   about 10 to about 20 percent of water; and
   about 1 to about 3 percent of calcium acetate.

25. The dosage form of claim 11, comprising by weight:
   about 0.5 to about 5.0 percent famotidine;
   about 60 to about 70 percent polyethylene glycol having an average molecular weight of about 400;
   about 10 to 20 percent water;
   about 2 to about 10 percent sodium acetate;
   about 0.5 to about 1.5 percent sodium stearate; and
   about 0.05 to about 0.3 percent poloxamer.

26. A method of delivering a pharmaceutical comprising the oral administration of the composition of claim 1.

* * * * *